US00PP37377P2

(12) United States Plant Patent
Hong et al.

(10) Patent No.: US PP37,377 P2
(45) Date of Patent: Apr. 21, 2026

(54) ***ILEX* PLANT NAMED 'GUARD'**

(50) Latin Name: ***Ilex dabieshanensis* x *latifolia***
Varietal Denomination: GUARD

(71) Applicant: Institute of Botany, Jiangsu Province and Chinese Academy of Sciences, Nanjing (CN)

(72) Inventors: Chen Hong, Nanjing (CN); Zhou Ting, Nanjing (CN); Chong Xinran, Nanjing (CN); Li Naiwei, Nanjing (CN); Lu Bo, Nanjing (CN); Zhou Yanwei, Nanjing (CN); Cai Xiaolong, Nanjing (CN); Lu Xiaoqing, Nanjing (CN); Wang Chuanyong, Nanjing (CN)

(73) Assignee: Institute of Botany, Jiangsu Province and Chinese Academy of Sciences

( * ) Notice: Subject to any disclaimer, the term of this patent is extended or adjusted under 35 U.S.C. 154(b) by 0 days.

(21) Appl. No.: 19/325,059

(22) Filed: Sep. 10, 2025

(51) Int. Cl.
*A01H 5/00* (2018.01)
*A01H 6/00* (2018.01)

(52) U.S. Cl.
USPC ..... Plt./247

(58) Field of Classification Search
USPC ..... Plt./247
See application file for complete search history.

(56) References Cited

U.S. PATENT DOCUMENTS

PP35,806 P2 * 5/2024 DeVries ..... Plt./247

* cited by examiner

*Primary Examiner* — Susan McCormick Ewoldt
*Assistant Examiner* — Zachariah Allan Kay

(57) ABSTRACT

A new and distinct cultivar of *Ilex* plant named 'GUARD' is disclosed characterized by an upright plant form with a dense crown and semi-open base. Fruits are bright red and occur in terminal clusters. Young stems are uniquely colored Red-Purple 63A. Foliage is elliptic with prominent veins and colored Yellow-Green 152D when young. The new variety is useful as an ornamental plant.

3 Drawing Sheets

Latin name of the genus and species: *Ilex dabieshanensis* x *latifolia*.

Variety denomination: 'GUARD'.

BACKGROUND OF THE INVENTION

The new cultivar, hereinafter referred to as 'GUARD', is the product of a planned breeding progam conducted in Nanjing, China. The seed parent is an unnamed, unpatented *Ilex dabieshanensis* K. Yao & M. B. Deng. The pollen parent is an unnamed, unpatented *Ilex latifolia* Thunb. The crossing resulting in the new cultivar 'Guard' was made during April of 2014 at a botanic garden in Nanjing, China. The inventors selected the new variety at a botanic garden in Nanjing, China in the October of 2018.

First asexual propagation of 'GUARD' by semi-softwood cuttings was made at the same botanic garden in July of 2019. The inventors continued controlled testing and propagation, assessing stability of the unique characteristics of this variety. At least four generations have been reproduced and have shown that the unique features of this cultivar are stable and reproduced true to type.

SUMMARY OF THE INVENTION

The cultivar 'GUARD' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'GUARD'. These characteristics in combination distinguish 'GUARD' as a new and distinct *Ilex* cultivar:

1. Upright plant with a dense crown and semi-open base.
2. Unique red-purple color of the new stem growth.
3. Distinct Yellow-Green 152D color of young foliage.
4. Elliptic leaf shape with prominent veins.
5. Bright red fruit, occurring in terminal clusters.

COMPARISON TO PARENT VARIETIES

*Ilex* 'GUARD' differs from the seed parent in the following:

1. New stem growth of 'Guard' is colored near Red-Purple 63A; new stem growth of the seed parent is colored Yellow-Green 145A.
2. Plants of 'Guard' are upright and dense; plants of the seed parent are less dense, and open.
3. Foliage shape of 'Guard' is elliptic; foliage shape of the seed parent is broad elliptic.
3. Mature foliage color of 'Guard' is Yellow-Green 146A; foliage color of the seed parent is Green NN137A.

*Ilex* 'GUARD' differs from the pollen parent in the following:

1. Plants of 'Guard' are upright and dense; plants of the pollen parent are less dense, and much more open.
2. Foliage shape of 'Guard' is elliptic; foliage shape of the pollen parent is oblong.
3. Foliage length of 'Guard' is 6.5 to 7.5; foliage length of the pollen parent varies from 8 to 19 cm.
4. The main vein on foliage of 'Guard' is more prominent than the main vein of the pollen parent.

5. Mature foliage color of 'Guard' is Yellow-Green 146A; foliage color of the pollen parent is Green 137A.

COMMERCIAL COMPARISON

*Ilex* 'GUARD' can be compared to the commercial variety of *Ilex meserveae* 'HACH1', U.S. Plant Pat. No. 25,475. Plants are similar in most horticultural characteristics, including upright plant habit and a distinct new stem coloration; however, plants of the new variety differ in the following:

1. 'Guard' produces new stems colored Red-Purple 63A; 'HACH1' produces new stems colored Greyed-Purple N186C.
2. Mature foliage color of 'Guard' is Yellow-Green 146A; mature foliage color of 'HACH1' is between Green 137A and Yellow-Green 147A.
3. 'Guard' is a female selection, producing berries' 'HACH1' is a male selection, not producing berries.

*Ilex* 'GUARD' can be compared to the commercial variety *Ilex verticillata* 'DD-21', U.S. Plant Pat. No. 35,806. Plants are similar in most horticultural characteristics; however, plants of the new variety differ in the following:

1. 'Guard' produces new stems colored Red-Purple 63A; 'DD-21' produces new stems colored Yellow-Green 144A.
2. Mature foliage color of 'Guard' is Yellow-Green 146A; mature foliage color of 'DD-21' is a mix of Green 138B and Yellow-Green 147C.
3. Young foliage color of 'Guard' is Yellow-Green 152A; young foliage color of 'DD-21' is Yellow-Green 147B.
4. Plants of 'Guard' are approximately 50% the width of plants of 'DD-21'.

BRIEF DESCRIPTION OF THE PHOTOGRAPHS

The accompanying photographs illustrate in full color a typical plant of 'GUARD' grown outdoors in the ground in Nanjing, China.

Figure 1:
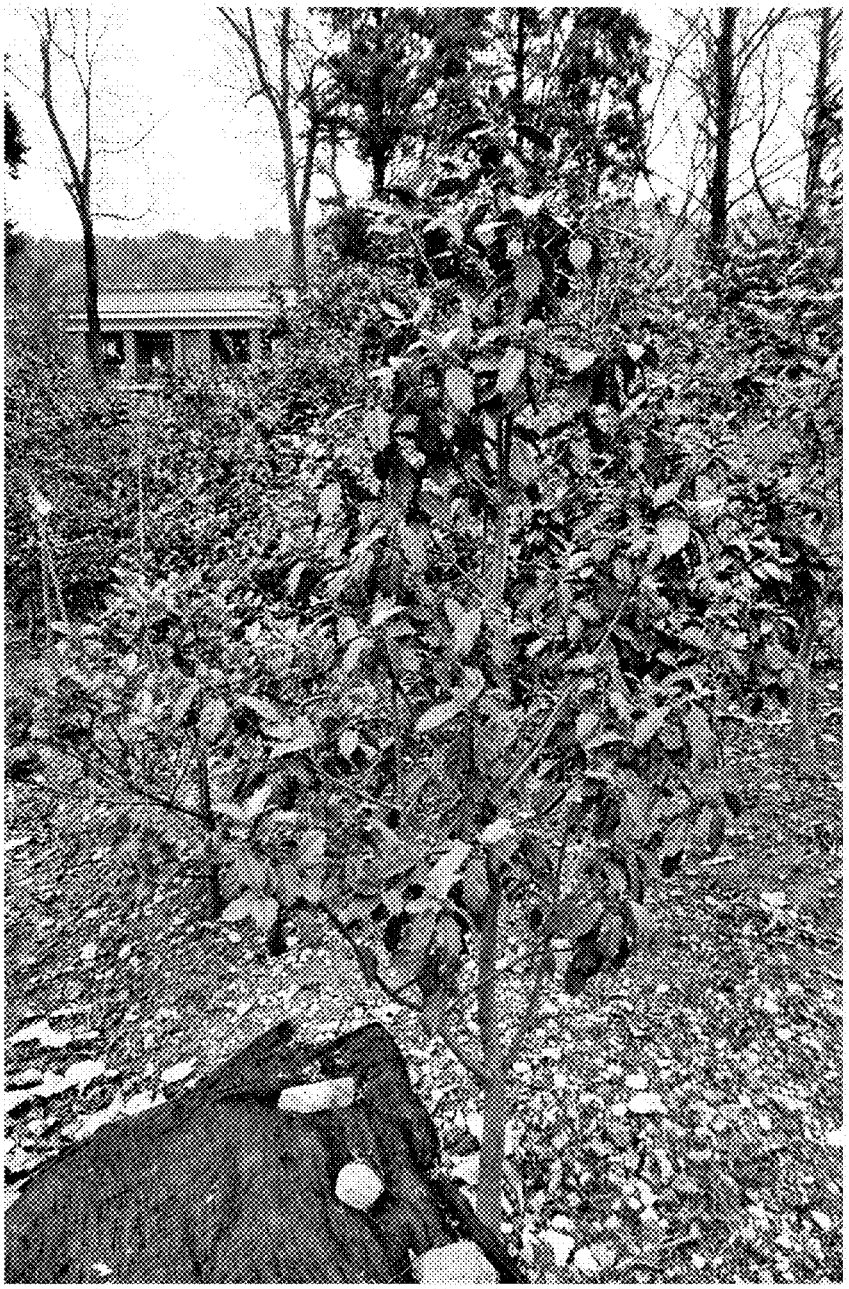
FIG. 1 is a fruiting plant of approximately 7 years old.
Figure 2:
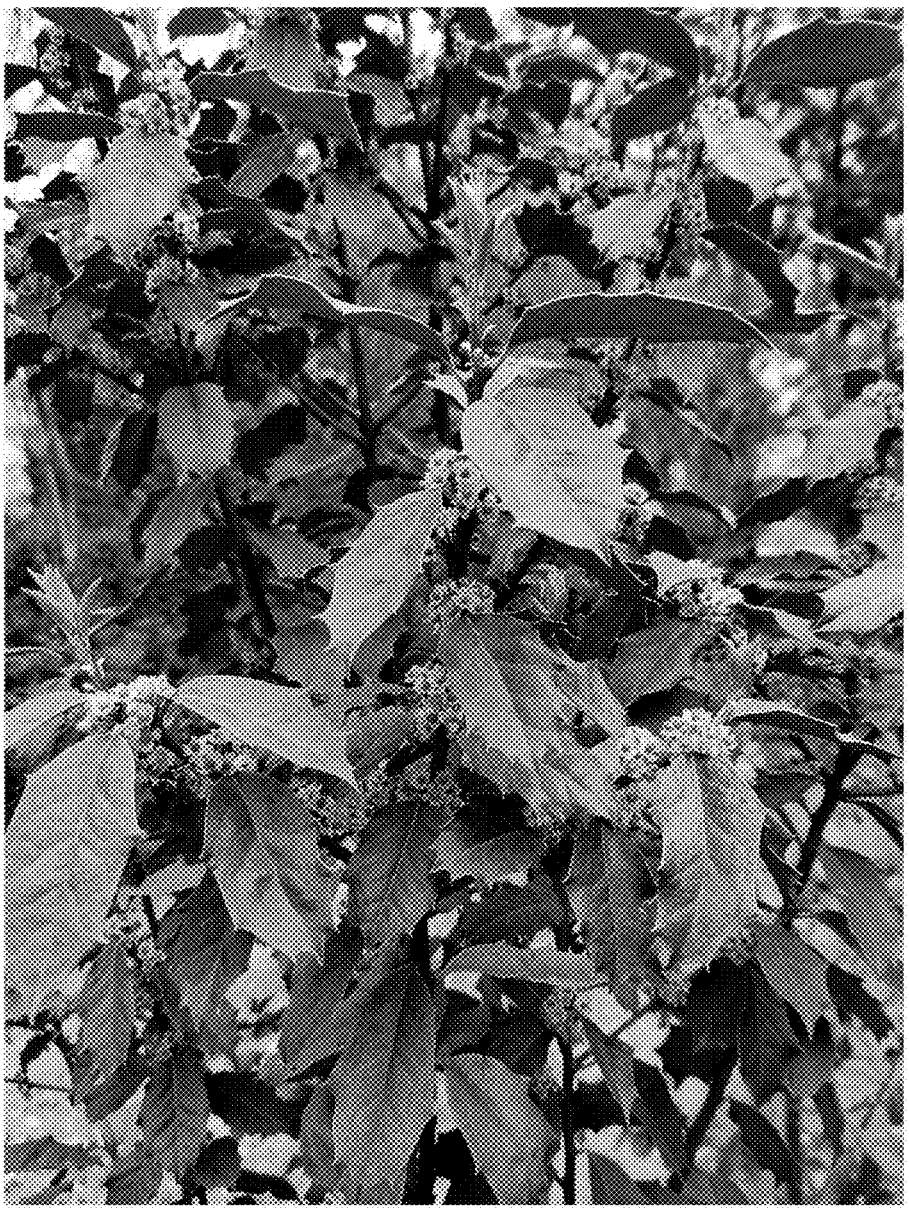
FIG. 2 illustrates the same plant while flowering.
Figure 3:
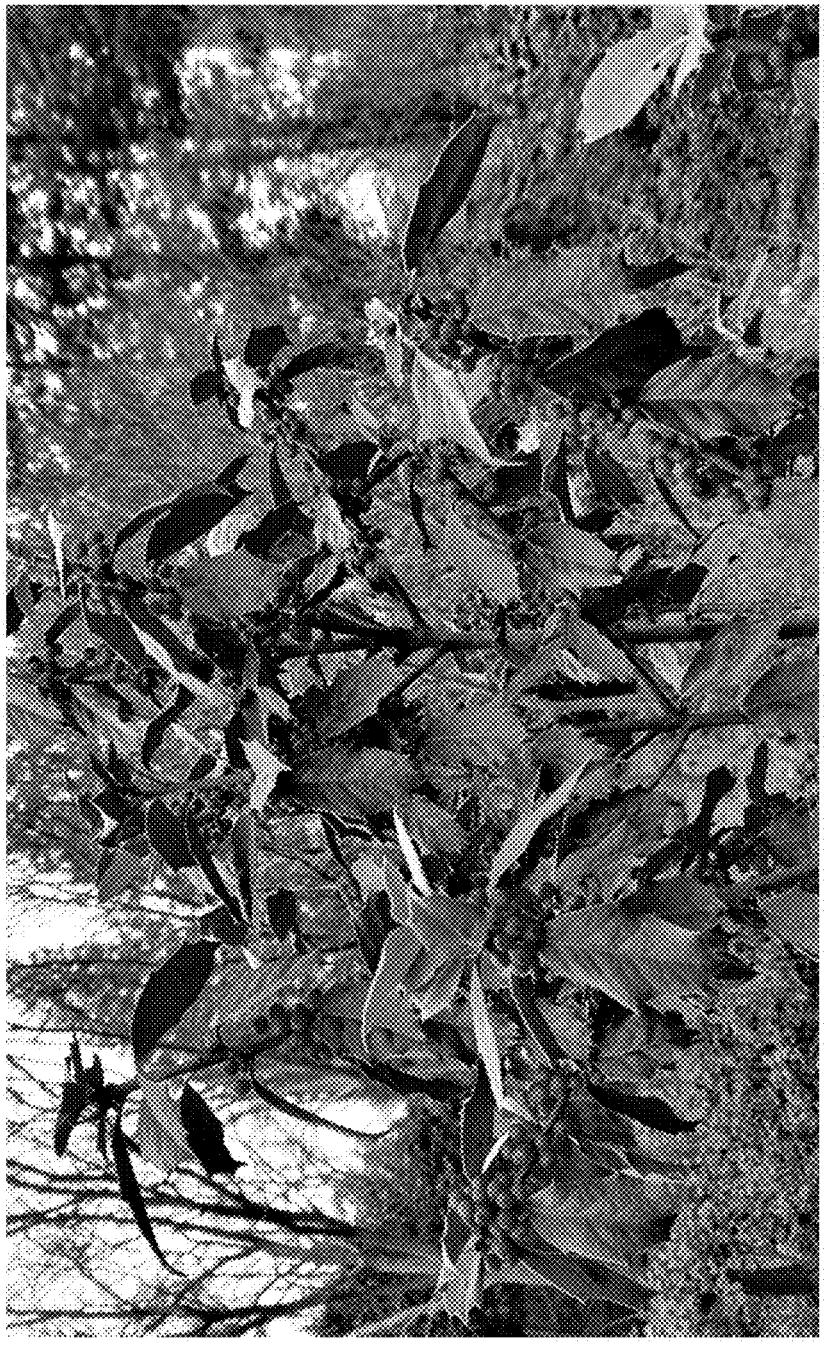
FIG. 3 is a closer view of the fruiting branches.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'GUARD' plants grown outdoors in Nanjing, China. Temperatures ranged from about 0° C. to 40° C. during the day and −5° C. to 30° C. at night. Plants are approximately 9 years old, and planted in the ground. Measurements and numerical values represent averages of typical plant types.

Botanical classification: *Ilex dabieshanensis* x *latifolia* 'GUARD'.

PROPAGATION

Typically by semi-hardwood cuttings in Spring and Summer.

Root description: Semi-woody, moderately dense roots. Colored near RHS Grey-Brown 199A.

PLANT

Growth habit: Upright plant with a dense crown and semi-open base.

Height: Approximately 190 cm.

Plant spread: Approximately 60 to 65 cm.

Branching characteristics: 3 primary branches each with 4 secondary lateral branches. No pinching required for lateral branch formation.

Lateral branches:

*Length*.—Average range 40 cm to 50 cm.
*Diameter*.—10 to 13 mm.
*Internode length*.—10 to 17 mm.
*Shape*.—Round.
*Aspect*.—Straight, 30° to 40° from center.
*Texture*.—Glabrous.
*Strength*.—Very strong, resists breakage, non-brittle.
*New growth color*.—Red-Purple 63A.
*Mature color*.—Yellow-Green 148A.

Other: Lenticels not observed. Oldest basal stem is colored near Greyed-Brown 199A.

FOLIAGE

Leaf:

*Arrangement*.—Single, alternate whorled.
*Density*.—Moderately dense.
*Average length*.—Approximately 6.5 to 7.5 cm.
*Average width*.—Approximately 3.8 to 4.2 cm.
*Shape of blade*.—Elliptic.
*Apex*.—Acute.
*Base*.—Mid-cuneate.
*Attachment*.—Stalked.
*Margin*.—Finely serrate.
*Aspect*.—Flat to very slightly undulate.
*Texture of top surface*.—Glabrous.
*Texture of bottom surface*.—Glabrous.
*Appearance of top surface*.—Leathery.
*Appearance of bottom surface*.—Matte.
*Color*.—Young foliage upper side: Yellow-Green 152D. Young foliage under side: Yellow-Green 152C. Mature foliage upper side: Yellow-Green 146A. Mature foliage under side: Yellow-Green 146D.
*Venation*.—Type: Pinnate. Venation color upper side: Yellow-Green 144B. Venation color under side: Yellow-Green 144B.

Petiole:

*Average length*.—Approximately 7 to 9.5 mm.
*Diameter*.—Approximately 2 mm.
*Color*.—Yellow-Green 146C upper and lower surfaces.

FLOWER

Axillary flowers, mostly occurring at stem terminus. Flowering begins around late March to early April in Nanjing, China. Typically flowering around 3 weeks. Individual flowers last about 5 to 7 days. Self-cleaning.

Flower size:

*Diameter*.—10 to 11 mm.
*Depth*.—5.6 to 6.5 mm.

Petals:
*Petal arrangement*.—Cruciform.
*Length*.—4.7 to 5.6 mm.
*Width*.—2.8 to 3.7 mm.
*Shape*.—Obovate.
*Margin*.—Entire.
*Apex*.—Obtuse.
*Base*.—Broad cuneate.
*Petal quantity*.—4.
*Texture*.—Glabrous all surfaces.
*Appearance*.—Matte all surfaces.
*Color*.—When opening: Upper surface: Yellow-Green 151A. Lower surface: Yellow-Green 151A. Fully opened: Upper surface: Yellow-Green 151A. Lower surface: Yellow-Green 151A.

Bud:
*Shape*.—Ellipsoid.
*Length*.—Approximately 4 mm.
*Diameter*.—Approximately 3 mm.
*Color*.—Yellow-Green 151A.

Sepals:
*Quantity*.—4.
*Length*.—0.5 mm.
*Width*.—0.3 mm.
*Shape*.—Deltate.
*Color*.—Interior Surface: Yellow-Green 151A. Exterior Surface: Yellow-Green 151A.
*Texture*.—All surfaces glabrous.

Fragrance: None detected.

Peduncle:
*Length*.—4.7 to 5.6 mm.
*Diameter*.—1 mm.
*Color*.—Yellow-Green 144C.
*Texture*.—Glabrous.
*Strength*.—Moderate.
*Angle*.—30° to 40° from attachment.

REPRODUCTIVE ORGANS

Gynoecium only:

Pistil:
*Number*.—1 per flower.
*Length*.—3.7 to 4.7 mm.
*Style length*.—3.3 to 3.7 mm.
*Stigma shape*.—Linear.
*Stigma color*.—Yellow-Green 151C.
*Ovary shape*.—Round.
*Ovary color*.—Yellow-Green 151C.

FRUIT AND SEED

Fruit:
*Type*.—Simple indehiscent berry.
*Shape*.—Globose.
*Length*.—7.5 to 8.5 mm.
*Width*.—8.5 to 9.5 mm.
*Color*.—RHS Red 43A. Immature fruit Yellow-Green 146A.
*Texture*.—Glabrous.

Seed: Seed production has not been observed.

OTHER CHARACTERISTICS

Disease and pest resistance: Neither resistance nor susceptibility to normal diseases and pests of *Ilex* observed.

Temperature tolerance: Observed cold tolerant to −8° C. Observed heat tolerant to 40° C.

What is claimed is:

1. A new and distinct cultivar of *Ilex* plant named 'GUARD' as herein illustrated and described.

* * * * *